(12) United States Patent
Martinez et al.

(10) Patent No.: US 6,189,536 B1
(45) Date of Patent: Feb. 20, 2001

(54) METHOD FOR PROTECTING IMPLANTABLE DEVICES

(75) Inventors: Gonzalo Martinez, Mendota Heights, MN (US); Markus Haller, Begnins (CH)

(73) Assignee: Medtronic Inc., Minneapolis, MN (US)

(*) Notice: Under 35 U.S.C. 154(b), the term of this patent shall be extended for 0 days.

(21) Appl. No.: 09/292,341

(22) Filed: Apr. 15, 1999

(51) Int. Cl.⁷ ................................................. A61B 5/00
(52) U.S. Cl. ................................. 128/897; 600/300
(58) Field of Search .......................... 128/897–899; 600/300

(56) References Cited

U.S. PATENT DOCUMENTS

| | | | |
|---|---|---|---|
| 4,381,981 | 5/1983 | Maes | 204/197 |
| 4,821,723 | 4/1989 | Baker et al. | 128/419 |
| 5,131,388 | 7/1992 | Pless et al. | 128/419 |
| 5,144,949 | 9/1992 | Olson | 128/419 |
| 5,158,078 | 10/1992 | Bennett et al. | 128/419 |
| 5,207,218 | 5/1993 | Carpentier et al. | 128/419 |
| 5,312,453 | 5/1994 | Shelton et al. | 128/419 |
| 5,314,430 | 5/1994 | Bardy et al. | 607/5 |
| 5,330,507 | 7/1994 | Schwartz | 607/14 |
| 5,331,966 | 7/1994 | Bennett et al. | 128/696 |
| 5,354,316 | 10/1994 | Keimel | 607/15 |
| 5,407,549 | 4/1995 | Camp | 204/196 |
| 5,545,186 | 8/1996 | Olson et al. | 607/14 |
| 5,660,728 | 8/1997 | Saaski et al. | 210/251 |
| 5,702,618 | 12/1997 | Saaski et al. | 216/2 |
| 5,705,070 | 1/1998 | Saaski et al. | 210/446 |

*Primary Examiner*—Max Hindenburg
(74) *Attorney, Agent, or Firm*—Thomas F. Woods; Michael J. Jaro; Harold Patton

(57) ABSTRACT

A pulse waveform is provided to at least one surface of an implantable device to protect it from corrosion from a corrosive fluid. The pulse waveform can be delivered through ether anodic or cathodic monophasic or asymetrical biphasic pulses using one electrode and an indiferent or sacrificial electrode. The electrode and the indiferent or sacrificial electrode are oriented such that a closed circuit between the two electrodes is completed through the corrosive fluid and the surface to be protected is within the completed circuit path.

17 Claims, 2 Drawing Sheets

METHOD FOR PROTECTING IMPLANTABLE DEVICES

FIELD OF THE INVENTION

The present invention relates to a method for protecting implantable devices from corrosion once the device is implanted, such as within a human body.

BACKGROUND

In many medical situations, it is desirable and often necessary to implant relatively small (micro) electromechanical devices for an extended period of time. For example, it may be desirable to continually administer fluid medication (either as a gas or a liquid) to a patient over an extended period of time. Examples of such treatments included the low dose continual administration of morphine for pain control, the administration of FUDR for cancer chemotherapy, the administration of baclofen for the treatment of intractable spasticity, and the like.

In such instances, a particularly desirable goal is to maintain a relatively constant level of medication in the patient's bloodstream. In order to accomplish this goal, relatively small fluid handling devices are implanted within a patient's body. However, both the medication and bodily fluids that may contact the micro fluid handling devices are typically corrosive. Thus, it is desirable to provide a corrosion-resistant layer to at least one surface of the micro fluid-handling device to prevent or limit corrosion. For example, Saaski et al. describe that a nominal layer of a corrosion-resistant substance may be deposited on a substrate by sputtering by using an e-beam evaporator, where suitable corrosion-resistant substances may be silicon, gold, platinum, chrome, titanium, zirconium, and oxides of silicon or these metals. It is further described that oxides may be formed by thermally oxidizing the corrosion-resistant substance in air after it has been applied to the substrate. See, U.S. Pat. Nos. 5,660,728; 5,702,618; and 5,705,070 all to Saaski et al.

SUMMARY OF THE INVENTION

What is yet needed is a method for protecting implantable devices from corrosion on at least one surface of the device, wherein that surface may or may not include a separate coating. For example, in a typical device fabrication process, a corrosion-resistant coating is applied to individual components along the fabrication process but prior to complete assembly of the device. Because typical coating methods utilize relatively high temperatures, coating a completely assembled device is generally not possible because the relatively high coating temperatures tend to be detrimental to electrical components which, in turn, ultimately adversely affects the functioning of the device.

Accordingly, one aspect of the present invention provides a method for protecting an implantable device from corrosion that includes providing a pulse waveform to at least one surface of the implantable device, thus eliminating the need to apply a separate coating to prevent corrosion.

However, if a coating is to be applied to a device, providing a pulse waveform to at least one surface including a coating of the implantable device can protect the device from corrosion that may occur through very small openings in the coating or through coating imperfections.

As used herein, "corrosion" refers to a complex electrochemical degradation of a conductive material (such as a metal or a metal alloy) or a semiconductive material (such as silicon or carbon) due to a reaction between such materials and the environment, usually an aqueous electrolyte-containing environment, such as an acidic or basic (alkaline) environment. In general, a corrosion product of such a material is in the form of an oxide of the material, such as a metal oxide, silicon dioxide, and the like. While not wishing to be bound by any particular theory, it is believed that corrosion occurs when the material (such as copper or silicon) contacts an electolytic solution and a mini-electrochemical circuit is formed when a small amount of the material dissolves in the water and combines with dissolved species. In forming the mini-electrochemical circuit, an imbalance of electrons between the solution and the surrounding material creates a minute flow of electrons, or current. So long as a current is allowed to flow, the material will continue to deteriorate, resulting in degradation and even pitting of the material.

A "corrosive fluid" is one that participates in the corrosion of a material. Typical corrosive fluids are aqueous solutions containing electrolytes that generally have an alkaline pH (i.e., greater than about 7.0). For example, a corrosive fluid can be a solution of a therapeutic agent (e.g., baclofen) or even a bodily fluid, such as blood.

A method in accordance with the present invention is suitable for any implantable device but is particularly well suited for micro electromechanical devices, such as implantable pumps, filters, valves, cardiac pacesetters, lead conductors and electrodes, prosthetic device, to name a few.

Thus, one aspect of the present invention provides a method for protecting an implantable device from a corrosive fluid comprising providing a pulse waveform to at least one surface of the implantable device, wherein a closed circuit is completed though the corrosive fluid. Preferably, the pulse waveform originates from at least one electrode on the at least one surface of the implantable device. The pulse waveform preferably has a frequency of about 100 KHz to about 1 MHz. The pulse waveform is preferably generated by a current having a voltage of about 1 volt to about 10 volts.

In one embodiment, the pulse waveform generated in the surface has a root mean squared of current of about 8.6 mA to about 0.029 mA, wherein the surface comprises silicon. However, one with skill in the art will recognize that the magnitude of the current may be dependent on the material to be protected and the composition of the corrosive fluid. Thus, some materials may require more or less current to shift them to a region of stability, as described herein.

The method may also include a second electrode, wherein the closed circuit is completed though the corrosive fluid from the at least one electrode and the second electrode. Therefore, the at least one surface of the implantable device is preferably located between the at least one electrode and the second electrode.

The at least one electrode is preferably formed from a material selected from the group consisting of a metal, a metalloid, and a combination thereof. Alternatively, the at least one electrode comprises a material having an electrical conductivity of at least $10^{-6}$ mho/cm. More preferably, the at least one electrode comprises a metal selected from the group consisting of a refractory metal, a noble metal, and a combination thereof, including an alloy, a nitride, and an oxide of each. Even more preferably, the metal is selected from the group consisting of tantalum, titanium, zirconium, ruthenium, iridium, platinum, and a combination thereof.

In accordance with the present invention, the implantable device is preferably selected from the group consisting of a pacemaker, a pacemaker-cardioverter-defibrillator, an implantable neurostimulator, a muscle stimulator, an implantable monitoring device, an implantable fluid handling device, a defibrillator, a cardioverter/defibrillator, a gastric stimulator, a drug pump, and a hemodynamic monitoring device. In one embodiment of the present invention, the at least one surface of the implantable device is an exterior surface of the implantable device. In another embodiment, the at least one surface of the implantable device comprises an interior surface of the implantable device, however a combination of surface can be protected by a method in accordance with the present invention.

The corrosive fluid can be selected from the group of an aqueous solution of a therapeutic agent or a body fluid.

Another aspect of the present invention provides an implantable device comprising a first electrode attached to a surface of the implantable device and a second electrode each operatively connected to a waveform generator, wherein the second electrode is oriented such that the surface of the implantable device is between the first electrode and the second electrode upon completion of a closed circuit.

The surface of the implantable device may also include a coating selected from the group consisting of a natural hydrogel, a synthetic hydrogel, silicone, polyurethane, polysulfone, cellulose, polyethylene, polypropylene, polyamide, polyimide, polyester, polytetrafluoroethylene, polyvinyl chloride, epoxy, phenolic, neoprene, polyisoprene, and a combination thereof.

BRIEF DESCRIPTION OF THE DRAWINGS

These and other features of the present invention will become readily apparent upon reference to the drawings.

DETAILED DESCRIPTION

The present invention is directed to protecting an implantable device from corrosion by a corrosive fluid without the need for a separate coating. Preferably, a method in accordance with the present invention includes providing a pulse waveform to at least one surface of the implantable device. The pulse waveform can be delivered through either anodic or cathodic pulses.

Figure 1:
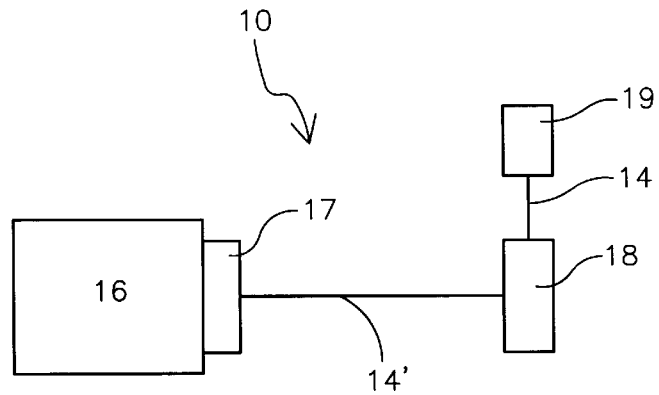
FIG. 1 a schematic diagram showing a system for protecting an implantable device from corrosion in accordance with the present invention.

FIG. 1 is a schematic illustration showing a system 10 in accordance with the present invention for protecting an implantable device from corrosion. Generally, an implantable device 16 includes a first electrode 17 that is affixed to at least one surface of the implantable device 16. Preferably, the first electrode 17 is affixed to the surface of the implantable device that is to be protected in accordance with the present invention. The first electrode 17 is operatively connected to a pulse waveform generator 18 by connector trace 14'. A second electrode 19, sometimes referred to as a sacrificial or indifferent electrode, is operatively connected, preferably electrically connected by connector trace 14, to the pulse waveform generator 18.

Any of the electrodes, connectors, and traces can be affixed to a surface of an implantable device by conventional techniques, such as sputtering, bonding, screen printing, plating, thermally depositing, or applied by any suitable dry or wet deposition process as is known in the art. Interconnection to a current or voltage source (i.e., a waveform generator) is preferably made through insulated traces, such as via holes, microfeedthroughs, or any other conventional manner. For example, via holes in crystalline silicon can be fabricated by anistropically etching holes therethrough and then metalizing the holes.

Preferably, an electrode utilized in the present invention has a relatively large surface area. As used herein, "surface area" refers to the size of the exposed portion of the electrode, which includes both the dimension of the electrode (e.g., length, width, height) and the porosity of the electrode (which is a function of the type of the material used to form the electrode). However, maximizing the surface area should be balanced with the physical dimensions or geometry of the electrode. The geometry of the electrode should be relatively small while porosity should be increased so that the overall goal of the electrode is to minimize the current drain on the device. An electrode preferably has a dimension of about 1 to about 4 mm in length and about 1 to about 4 mm in width. However, the at least one electrode has a nominal thickness so that the presence of the electrode on an implantable device will not substantially increase the overall size of the implantable device. Thus, the at least one electrode preferably has a thickness from about 25 microns to about 2 mm.

The surface area is related to the porosity of the material forming the electrode, with highly porous materials being preferred. Preferable materials are conductive or semiconductive materials. More preferable materials are those having an electrical conductivity of at least $10^{-6}$ mho/cm. Even more preferable, the material is selected from the group consisting of a metal, a metalloid, and a combination thereof. Most preferable, the material is a metal selected from the group consisting of a refractory metal, a noble metal, as well as an alloy, a nitride, and an oxide thereof, and a combination thereof. Suitable metals include those selected from the group consisting of tantalum, titanium, ruthenium, iridium, platinum, as well as an alloy, a nitride, and an oxide thereof, and a combination thereof.

Figure 2:
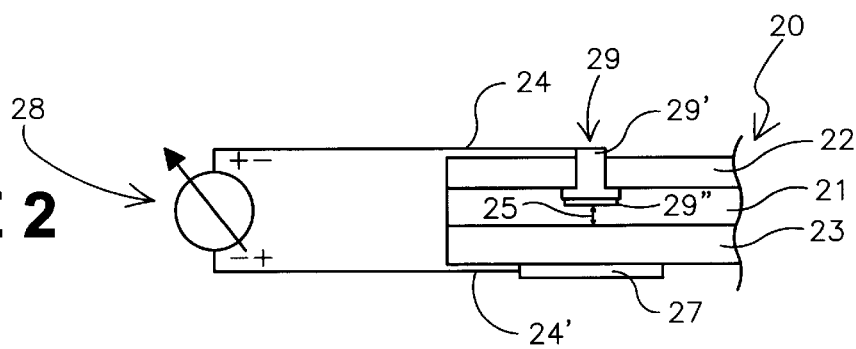
FIG. 2 is a schematic diagram of an embodiment for protecting an implantable device from a corrosive fluid in accordance with the present invention.

FIG. 2 illustrates one embodiment for protecting an implantable device from corrosion by a corrosive fluid in accordance with the present invention. In this embodiment, the implantable device includes a reservoir 21 formed between a first surface 23 and a second surface 22. The reservoir 21 typically contains an aqueous solution of a therapeutic agent, such as a chemotherapeutic agent, an analgesic agent, etc., for in vivo delivery. The system 20 includes a current or voltage control element 28 (i.e. a waveform generator) operatively connected to a first electrode 29 and a second electrode 27 by insulated conductive traces 24 and 24', respectively. The second electrode 27, sometimes referred to as a sacrificial electrode, is preferably arranged so that a surface, shown as the first surface 23, to be protected from corrosion in accordance with the present invention is between the first electrode 29 and the second electrode 27. In this instance, the surface 23 is an interior surface, i.e., a surface of the implantable device that is directly exposed to body fluids after implantation. The first electrode 29 includes an insulated portion 29' and an exposed electrode portion 29", wherein the insulated portion 29' has a conductive feedthrough which electrically connects the exposed electrode portion 29" to the conductive trace 24. Preferably, the first electrode 29 is attached to one side of an insulated layer 22 (e.g., such that commercially available under the trade designation PYREX) to prevent short circuiting. The first electrode 29 and the second electrode 27 are preferably a cathode and an anode, respectively, although the opposite orientation is also contemplated. One with ordinary skill in the art will readily appreciate that the elements in the FIG. 2 schematic may take a variety of forms.

Generally, in operation, a waveform is impressed either a) anodically to form or maintain a stable oxide, preferably in a material such as tantalum, titanium, niobium, zirconium, and the like (including alloys and oxides thereof); or b) cathodically to shift the corrosion potential of the device material to a region of increased thermodynamic stability.

The closed circuit is completed through the corrosive fluid, indicated by arrow 25. For example, the device could be protected by impressing a negative current so that the second electrode 27 (a cathode in this embodiment) directly bonded to the surface 23 of the implantable device to be protected shifts the corrosion potential of the implantable device surface to a stable region (i.e., reducing oxidation) while the first electrode 29 (an anode in this embodiment and is a sacrificial electrode) is oxidized but its oxide remains adhered to the stucture. The material of the second electrode 27 in this instance is selected for its good corrosion resistance, good electrical conductor and bonding affinity to the structure (in this case, surface 23). Preferably, the first electrode 29 can be made of a metal selected from the group consisting tantalum, titanium, and ruthenium. Preferably, the second electrode 27 can be made of a material selected from the group consisting of platinum, ruthenium, and iridium, including an alloy or oxide thereof.

Figure 2A:
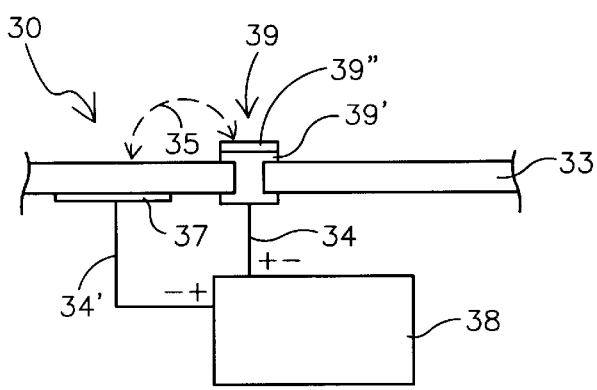
FIG. 2A is a schematic diagram of another embodiment for protecting an implantable device from a corrosive fluid in accordance with the present invention.

Referring to FIG. 2A, another embodiment of protecting an implantable device in accordance with the present invention is shown. In this embodiment, the implantable device includes a system 30 for protecting at least one surface 33 from corrosion by a corrosive fluid. The system 30 includes a current control element 38 operatively connected to a first electrode 39 and a second electrode 37 by conductive traces 34 and 34', respectively. The second electrode 37 is preferably arranged so that a surface, shown as the surface 33, to be protected from corrosion in accordance with the present invention is between a closed circuit from the first electrode 39 and the second electrode 37, shown as arrow 35 through a corrosive fluid. In this embodiment, the corrosive fluid can be a body fluid and the surface 33 can be an exterior surface, i.e., a surface of the implantable device that is exposed to body fluids after implantation. The first electrode 39 includes an insulated portion 39' and an exposed electrode portion 39", wherein the insulated portion 39' has a conductive feedthrough which conductively connects the exposed electrode portion 39" to the conductive trace 34. The first electrode 39 and the second electrode 37 are preferably a cathode and an anode, respectively, although the opposite orientation is also contemplated. One with ordinary skill in the art will readily appreciate that the elements in the FIG. 2A schematic may take a variety of forms.

Preferably, a waveform is impressed using monophasic pulses with amplitudes of less than about 20 volts DC, more preferably from about 1 volt to about 10 volts. The waveform preferably has a frequency ranging from about 100 KHz to about 1 MHz, more preferably from about 10 KHz to about 1 MHz. Biphasic pulses could also be used provided that they are asymmetrical. For example, if cathodic protection is desired, then the cathodic portion (amplitude) of the biphasic is preferably higher that that of the reverse phase.

An implantable device may be any implantable device embodying a circuit as described herein. For example, in the case where the implantable device is a pacemaker, the implantable device may be a pacemaker such as that described in U.S. Pat. No. 5,158,078 to Bennett, et al.; U.S. Pat. No. 5,312,453 to Shelton et al.; or U.S. Pat. No. 5,144,949 to Olson et al.

Implantable device may also be a pacemaker-cardioverter-defibrillator (PCD) corresponding to any of the various commercially-available implantable PCDs. For example, the present invention may be practiced in conjunction with PCDs such as those described in U.S. Pat. No. 5,545,186 to Olson, et al.; U.S. Pat. No. 5,354,316 to Keimel; U.S. Pat. No. 5,314,430 to Bardy; U.S. Pat. No. 5,131,388 to Pless; or U.S. Pat. No. 4,821,723 to Baker, et al.

Alternatively, an implantable device may be an implantable neurostimulator or muscle stimulator such as that disclosed in U.S. Pat. No. 5,199,428 to Obel, et al.; U.S. Pat. No. 5,207,218 to Carpentier, et al.; or U.S. Pat. No. 5,330,507 to Schwartz, or an implantable monitoring device such as that disclosed in U.S. Pat. No. 5,331,966 to Bennett, et al.

Additionally, the implantable device may be micromachined devices such as implantable fluid handling devices for continuous administration of therapeutic agents including those for pain management, cancer chemotherapy, treatment of intractable spasticity, to name a few. Such devices are described in, for example, U.S. Pat. Nos. 5,705,070; 5,702,618; and 5,660,728 all to Saaski et al.

Further, for example, an implanted device may be a defibrillator, a cardioverter/defibrillator, a brain stimulator, a gastric stimulator, a drug pump, a hemodynamic monitoring device, or any other implantable device that would benefit from pulse waveform protection against corrosion. Therefore, the present invention is believed to find wide application in any form of implantable device. As such, the description herein making reference to any particular medical device is not to be taken as a limitation of the type of medical device that can be protected from corrosion as described herein.

As mentioned above, a method in accordance with the present invention can be utilized to protect an uncoated surface of an implantable device. Alternatively, a method in accordance with the present invention can be utilized to protect the substrate of a coated surface of an implantable device when discontinuities, pinholes, and the like, could cause corrosion. Typically, a surface of an implantable device is coated with a polymer selected from the group consisting of a natural hydrogel, a synthetic hydrogel, silicone, polyurethane, polysulfone, cellulose, polyethylene, polypropylene, polyamide, polyimide, polyester, polytetrafluoroethylene, polyvinyl chloride, epoxy, phenolic, neoprene, polyisoprene, and a combination thereof.

It is to be understood that an implantable device in accordance with the present invention may include an electrode on any surface to be protected from corrosion. For example, an electrode may be on an exterior surface of an implantable device to inhibit corrosion of the implantable device upon exposure to in vivo fluids, such as cardiac pacemakers, defibrilators, and the like. Additionally, an electrode may be on an interior surface of an implantable device to inhibit corrosion of the implantable device upon exposure to a fluid contained within the implantable device, such as implantable therapeutic agent delivery pumps. Consistent with a method in accordance with the present invention, an electrode can be provided both an interior surface and an exterior surface of an implantable device so long as a conductive path to each electrode is completed through the corrosive fluid in contact with each electrode. This will minimize the potential of a short circuit between the these two electrodes

EXAMPLES

While a method in accordance with the present invention has been described herein, the following non-limiting examples will further illustrate the invention.

Figure 3:
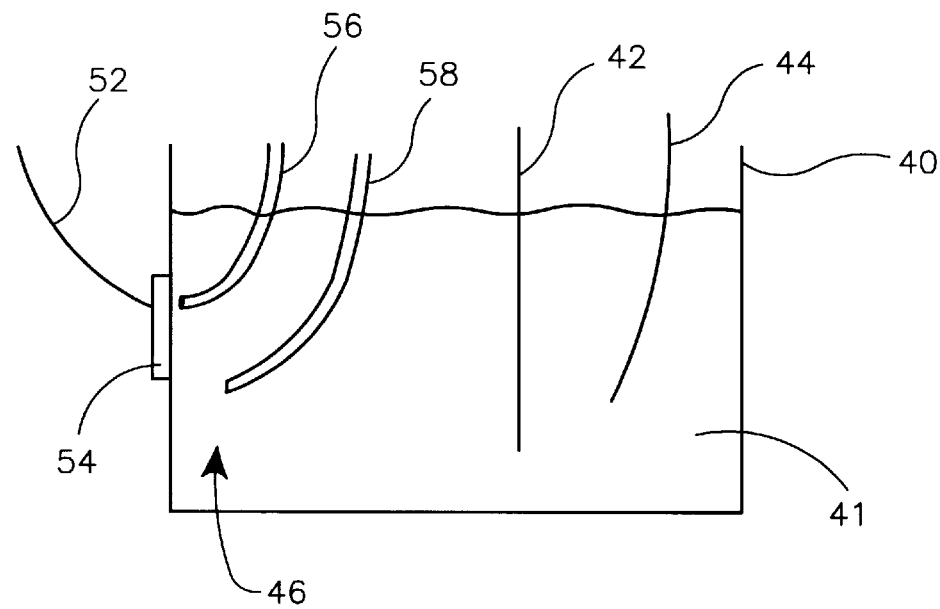
FIG. 3 is a schematic diagram of a configuration utilized in evaluating pulse waveform protection of a substrate as described in the Example.

To evaluate the use of an anode for cathodic protection of an implantable device, a saturated calomel electrode (a glass/mercury/chloride electrode) tested for its effect on a silicon doped boron substrate, a common material for implantable device fabrication—what portions of the device (although micromachined titanium or other metals could be used) in an alkaline buffer having a pH of 8.66. FIG. 3 illustrates the laboratory set-up for the evaluation.

The evaluation was conducted in a reservoir 40 containing an alkaline buffer 41 described above at a temperature of about 37 degrees C. The reservoir 40 included a partial partition 42, with a nitrogen gas supply 44 on one side of the partition and a conductive system 46 on the other side. Nitrogen gas was bubbled through the reservoir because to maintain the pH of the buffer solution stable.

A conductive system 46 included an electrical connection 52 to the waveform generator; a one inch (2.54 cm) flat coupon of p-type 100 silicon sample 54 exposed to the solution via a 1 cm OD orifice; a high porosity sintered platinum lead electrode 56 (commercially available under the trade designation Capture-Z, from Medtronic, Inc., Minneapolis, Minn.); and a saturated calomel electrode (SCE) 58 utilized to measure the corrosion potential of the sample to be protected.

The p-type 100 silicon sample was placed in solution and a series of monophasic pulses of about 10 V were applied at frequencies of about 10 Hz, 100 KHz, and 999 KHz. The root mean square of the total current was monitored and determined that the lowest current needed was at a frequency of about 1 MHz.

Figure 4:
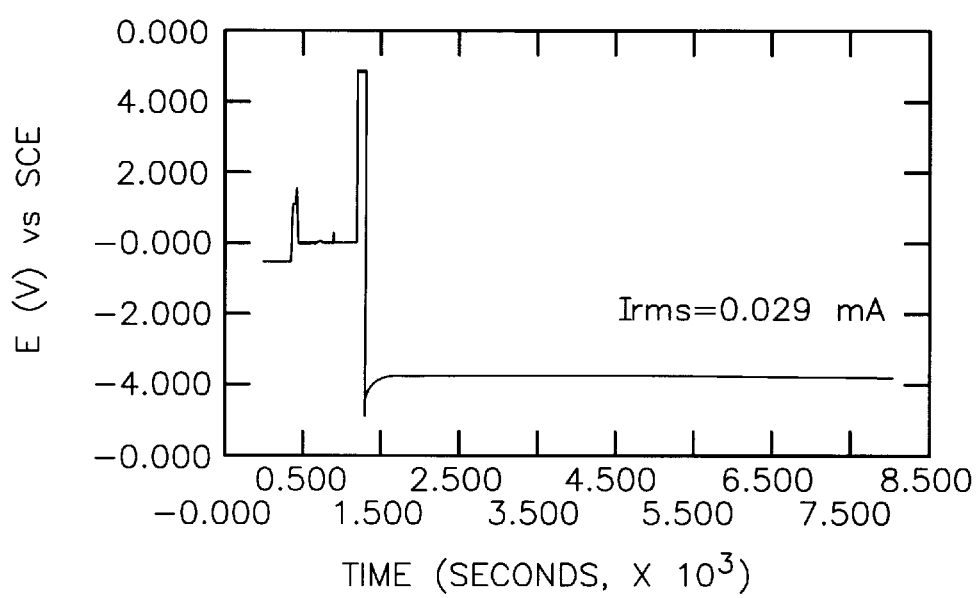
FIG. 4 is a graph indicating pulse waveform protection in a corrosive liquid as described in the Examples.

The graph of FIG. 4 illustrates that the current drain can be reduced to an average root mean squared current 29 microAmps by utilizing this anode and electrode design in combination with a monophasic waveform of 10 V DC and a frequency of 1 MHz. The sintered platinum porous electrode appeared to limit the reduction in current drain at higher frequencies. Further, there appeared to be a relatively large shift in the electrochemical potential (toward stable regions), shown by the relatively long plateau in the curve beginning just before 0.5 seconds along the x-axis and the absolute value of the corrosion potential (plotted as "E in Mv vs SCE" on the y-axis). It is believed that stabilization of the substrate coupled with a low current drain would be particularly useful for protecting surfaces formed form conductive materials (such as a metal or its alloy), semiconductive materials (such as silicon), or a combination thereof.

The complete disclosures of all patents, patent applications, and publications are incorporated herein by reference as if individually incorporated. The above disclosure is intended to be illustrative and not exhaustive. The description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached thereto.

What is claimed is:

1. A method for protecting an implantable medical device from a corrosive human biologic fluid of a patient, the implantable medical device comprising a hermetically sealed housing having a plurality of external surfaces, the housing having disposed therewithin means for delivering a therapy to the patient, the device being suitable for implantation within the patient, comprising providing a pulse waveform to at least one of the plurality of surfaces of the implantable device, wherein a closed circuit is completed though the corrosive fluid.

2. The method of claim 1 wherein the pulse waveform originates from at least one electrode on the at least one surface of the implantable device.

3. The method of claim 2 wherein the pulse waveform has a frequency of about 100 KHz to about 1 MHz.

4. The method of claim 2 wherein wherein the pulse waveform generates in one material a root mean squared of current of about 8.6 mA to about 0.029 mA.

5. The method of claim 2 wherein the pulse waveform is generated by a current having a voltage of about 1 volt to about 10 volts.

6. The method of claim 2 further comprising a second electrode, wherein the closed circuit is completed though the corrosive fluid from the at least one electrode and the second electrode.

7. The method of claim 6 wherein the at least one surface of the implantable device is located between the at least one electrode and the second electrode.

8. The method of claim 2 wherein the at least one electrode is formed from a material selected from the group consisting of a metal, a metalloid, and a combination thereof.

9. The method of claim 2 wherein the at least one electrode is comprises a material having an electrical conductivity of at least $10^{-6}$ mho/cm.

10. The method of claim 8 wherein the at least one electrode comprises a metal selected from the group consisting of a refractory metal, a noble metal, and a combination thereof, including an alloy, a nitride, and an oxide of each.

11. The method of claim 10, wherein the metal is selected from the group consisting of tantalum, titanium, zirconium, ruthenium, iridium, platinum, and a combination thereof.

12. The method of claim 2 wherein the implantable device is selected from the group consisting of a pacemaker, a pacemaker-cardioverter-defibrillator, an implantable neurostimulator, a muscle stimulator, an implantable monitoring device, an implantable fluid handling device, a defibrillator, a cardioverter/defibrillator, a gastric stimulator, a drug pump, and a hemodynamic monitoring device.

13. The method of claim 2 wherein the corrosive fluid is selected from the group of an aqueous solution of a therapeutic agent or a body fluid.

14. The method of claim 2 wherein the at least one surface of the implantable device comprises an exterior surface of the implantable device.

15. The method of claim 2 wherein the at least one surface of the implantable device comprises an interior surface of the implantable device.

16. An implantable medical device comprising a hermetically sealed housing having a plurality of external surfaces, the housing having disposed therewithin means for delivering a therapy to a patient, the device being suitable for implantation within a human biologic corrosive fluid of the patient, the device comprising a first electrode attached to one of the plurality of surfaces of the implantable device and a second electrode, each electrode being operatively connected to a waveform generator, wherein the second electrode is oriented such that the surface of the implantable device is disposed between the first electrode and the second electrode in respect of an electrical signal transmitted through a closed circuit that includes the first and second electrodes.

17. The implantable device of claim 16 wherein at least one of the plurality of surfaces of the implantable device comprises a coating selected from the group consisting of a natural hydrogel, a synthetic hydrogel, silicone, polyurethane, polysulfone, cellulose, polyethylene, polypropylene, polyamide, polyimide, polyester, polytetrafluoroethylene, polyvinyl chloride, epoxy, phenolic, neoprene, polyisoprene, and a combination thereof.

\* \* \* \* \*